United States Patent
Shah et al.

(10) Patent No.: US 10,517,869 B2
(45) Date of Patent: Dec. 31, 2019

(54) TOPICAL BRIMONIDINE TARTRATE OPHTHALMIC SOLUTION

(71) Applicant: SENTISS PHARMA PRIVATE LIMITED, New Delhi (IN)

(72) Inventors: Mandar V. Shah, New Delhi (IN); Deepak Bahri, New Delhi (IN)

(73) Assignee: SENTISS PHARMA PRIVATE LIMITED, New Delhi (IN)

( * ) Notice: Subject to any disclaimer, the term of this patent is extended or adjusted under 35 U.S.C. 154(b) by 0 days.

(21) Appl. No.: 15/107,576

(22) PCT Filed: Dec. 18, 2014

(86) PCT No.: PCT/IB2014/067066
§ 371 (c)(1),
(2) Date: Jun. 23, 2016

(87) PCT Pub. No.: WO2015/097600
PCT Pub. Date: Jul. 2, 2015

(65) Prior Publication Data
US 2016/0331745 A1    Nov. 17, 2016

(30) Foreign Application Priority Data
Dec. 24, 2013 (IN) .......................... 3763/DEL/2013

(51) Int. Cl.
| | | |
|---|---|---|
| *A61K 31/498* | (2006.01) | |
| *A61K 47/18* | (2017.01) | |
| *A61K 47/38* | (2006.01) | |
| *A61K 9/00* | (2006.01) | |
| *A61K 47/02* | (2006.01) | |

(52) U.S. Cl.
CPC .......... *A61K 31/498* (2013.01); *A61K 9/0048* (2013.01); *A61K 47/02* (2013.01); *A61K 47/186* (2013.01); *A61K 47/38* (2013.01)

(58) Field of Classification Search
CPC ...... A61K 31/498; A61K 47/02; A61K 47/18; A61K 47/38; A61K 9/00
See application file for complete search history.

(56) References Cited

U.S. PATENT DOCUMENTS

| | | |
|---|---|---|
| 6,627,210 B2 | 9/2003 | Olejnik et al. |
| 2009/0170944 A1* | 7/2009 | Lambert ............... A61K 9/0048 514/559 |
| 2010/0203165 A1 | 8/2010 | Horn |

FOREIGN PATENT DOCUMENTS

| | | |
|---|---|---|
| WO | 2010048586 A1 | 4/2010 |
| WO | 2011/027365 A2 | 3/2011 |
| WO | 2012144906 A1 | 10/2012 |
| WO | 2012150960 A1 | 11/2012 |
| WO | 2013086441 A2 | 6/2013 |

OTHER PUBLICATIONS

Barot et al. (2010) "Trends in Ophthalmic Preservatives: A Review," Drug Delivery Technology. 10(6):46-49.
International Search Report with Written Opinion corresponding to International Patent Application No. PCT/IB2014/067066, dated Jul. 1, 2015.
Jarver et al. (2011) "Peptide-mediated Cell and In Vivo Delivery of Antisense Oligonucleotides and siRNA," Molecular Therapy—Nucleic Acids, 1(6):1-17.
Spokoyny et al. (2013) "A Perfluoroaryl-Cysteine SNAR Chemistry Approach to Unprotected Peptide Stapling," Journal of the American Society, 135(16):5946-5949.
Zou et al. (2014) "Convergent diversity-oriented side-chain macrocyclization scan for unprotected polypeptides," 12(4):566-573.

* cited by examiner

*Primary Examiner* — Zohreh A Fay
(74) *Attorney, Agent, or Firm* — Lathrop Gage LLP; Brian C. Trinque; Benjamin A. Vaughan

(57) ABSTRACT

The present invention provides an aqueous ophthalmic composition comprising an alpha-2 adrenergic receptor agonist and a non-ionic cellulosic polymer, the solution having a pH less than 6.5. The present invention also provides an aqueous ophthalmic composition comprising an alpha-2 adrenergic receptor agonist and a benzododecinium halide. Also provided are methods of manufacture, use and method of reducing intraocular pressure in the patient in need thereof.

2 Claims, 2 Drawing Sheets

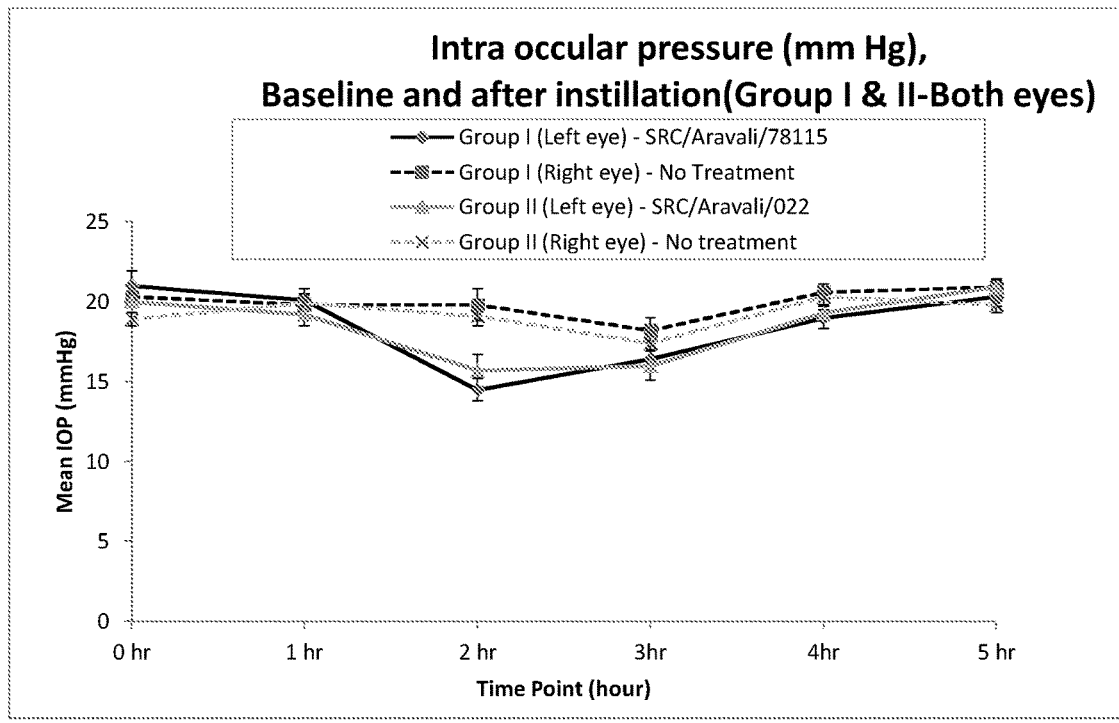
Figure I
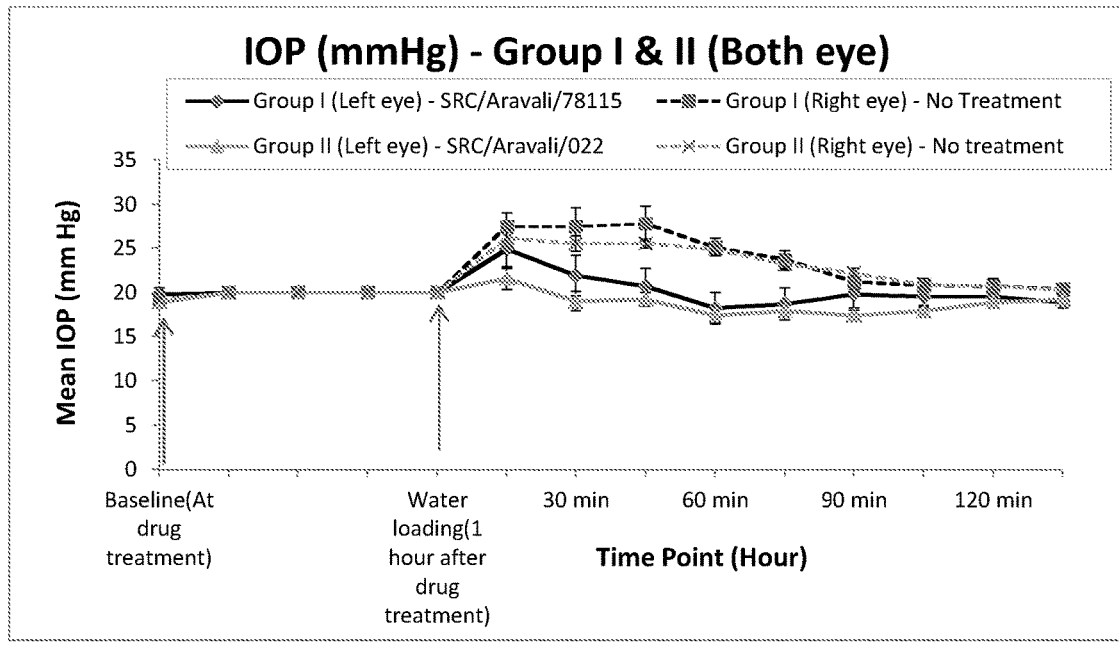
Figure II

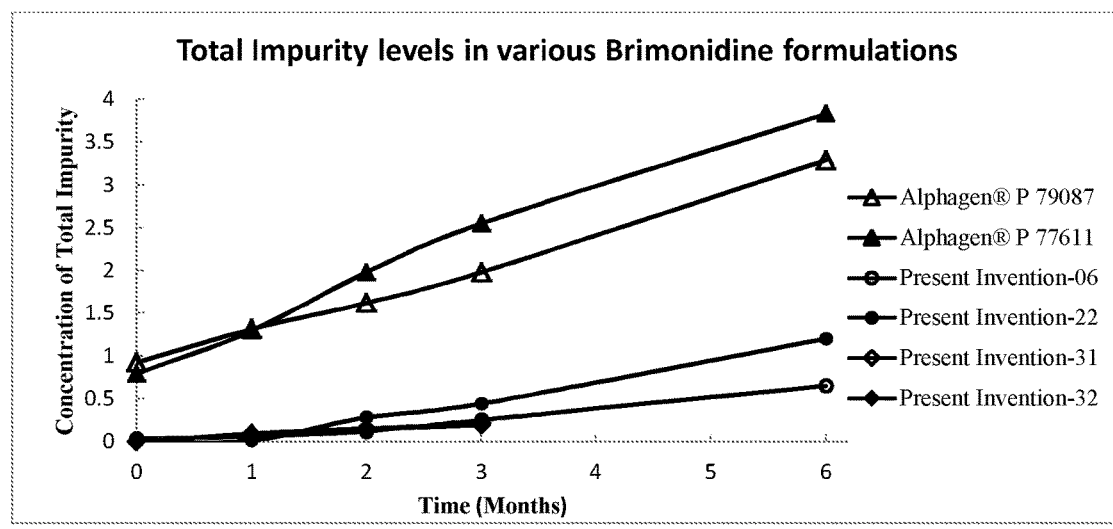
Figure III

TOPICAL BRIMONIDINE TARTRATE OPHTHALMIC SOLUTION

FIELD OF THE INVENTION

The present invention provides an aqueous ophthalmic composition comprising an alpha-2 adrenergic receptor agonist and a non-ionic cellulosic polymer, the solution having a pH less than 6.5. The present invention also provides an aqueous ophthalmic composition comprising an alpha-2 adrenergic receptor agonist and a benzododecinium halide. Also provided are methods of manufacture, use and method of reducing intraocular pressure in a patient in need thereof.

BACKGROUND OF THE INVENTION

The present invention provides a topical ophthalmic solution comprising an alpha-2 adrenergic receptor agonist such as brimonidine tartrate and/or pharmaceutically acceptable excipients wherein the ophthalmic solution is soluble enough to achieve therapeutic efficacy is soluble at a lower pH range of from about 5.5 to about 6.5.

The ophthalmic solution of the present invention contains from about 0.05% to about 0.2% (w/v) of brimonidine tartrate.

Brimonidine tartrate is an alpha-2-adrenergic agonist that reduces the elevated intraocular pressure (IOP) of the eye that is associated with glaucoma. The topical use of brimonidine to lower intraocular pressure in patients with glaucoma or ocular hypertension is known.

The first ophthalmic brimonidine product in the U.S. was approved by the FDA in 1996. That product, sold under the trade name Alphagan®, contained brimonidine in the form of brimonidine tartrate at a concentration of 0.2%. According to the product label, Alphagan® is adjusted (with NaOH or HCl) to a pH between 5.6 and 6.6, and further contains citric acid, polyvinyl alcohol, sodium chloride, sodium citrate, and purified water. The preservative contained in Alphagan® is benzalkonium chloride, the most widely used preservative for topical ophthalmic compositions.

In 2001, a second ophthalmic brimonidine product was approved by the U.S. FDA. This product, sold under the trade name Alphagan® P, contained brimonidine tartrate at two brimonidine concentrations, 0.15% and 0.1%, each of which is lower than the 0.2% brimonidine concentration in Alphagan®. Alphagan® P has a pH between 7.15 and 7.8, a range that is higher than that of Alphagan®. According to the product label, the lower concentration Alphagan® P formulation is sold at a pH of 7.4 to 8.0; the higher concentration is sold at a pH of 6.6 to 7.4. The preservative contained in Alphagan® P is chlorine dioxide. See U.S. Pat. Nos. 5,424,078 and 6,562,873. Alphagan® P also contains an anionic solubility enhancing component (carboxymethylcellulose) to help solubilize the brimonidine that is unionized at the pH of the compositions. Currently the innovator has discontinued marketing Alphagan®, the higher concentration, and low pH product.

Brimonidine has a pKa of 7.4. Hence, at pH below 6.6, it will be substantially ionized. For example, at a pH of 6.4, brimonidine is about 90% ionized. It is well known that ionized ophthalmic drugs have greatly reduced ocular permeability. It would have been expected that at a pH below 6.6 or 6.5, brimonidine would not permeate ocular tissue well, thereby reducing its efficacy compared to a higher pH product. It is believed that this is why the drug concentration in Alphagan® is substantially higher than in the higher-pH product Alphagan® P.

To overcome this disadvantage, the inventors of the present invention have formulated the current product with a non-ionic cellulose derivative, preferably hydroxypropyl methylcellulose (e.g., HPMC E4M grade). Without being bound by theory, it is believed that such a polymer reduces the surface tension to around 45 dynes/cm from about 72 dynes/cm, thereby helping to spread the drop more effectively around the ocular surface. Moreover, due to its viscosity, it is believed to increase retention of the drop in eye. Both of these effects are believed to help increase penetration of the drug. Surprisingly the efficacy of this invention appears to be similar to that of Alphagan® P, if not better (statistically significant), in spite of the present inventive compositions being at lower pH, wherein most of the drug is in ionized state.

The inventors of the present invention have formulated an ophthalmic solution wherein the pH of the formulation is acidic, preferably having pH from about 5.5 to about 6.5, yet is surprisingly effective compared to other low-pH products (e.g., Alphagan®). The lower pH also removes any need to use a solubility enhancing agent(s) because brimonidine is highly soluble at acidic pH (5.5-6.5) (though a solubility enhancing agent may be used if desired).

Further, the inventors of the present invention have surprisingly improved the stability of brimonidine significantly over the commercial product (Alphagan® P). The data are shown in Table 6.

Brimonidine tartrate has highly pH-dependent solubility. The solubility decreases sharply as the pH increases as shown in Table 1 (Refer U.S. Pat. No. 6,627,210 B2 page no. 13-14).

TABLE 1

Solubility of brimonidine tartrate a solubility enhancing agent over pH range of 5 to 8.

| Study 1 | | Study 2 | |
| --- | --- | --- | --- |
| pH | Solubility | pH | Solubility |
| 5.55 | ≥164.4 | 5.5 | ≥200.6 |
| 5.92 | 132.6 | 5.92 | 160.8 |
| 6.14 | 30.4 | 6.06 | 50.1 |
| 6.57 | 7.55 | 6.9 | 3.19 |
| 7 | 2.69 | 7.4 | 1.19 |
| 7.45 | 1.17 | 7.77 | 0.63 |
| 7.83 | 0.62 | 7.86 | 0.58 |
| | | 7.88 | 0.54 |

The original Alphagan® included a detergent preservative, benzalkonium chloride, which was known to be somewhat irritating to the eye.

Gasset and Grant et al. showed that BAC accumulates in ocular tissue and remains there for long periods, adversely affecting both the corneal surface and the conjunctiva. Therefore, cessation of the medications may not immediately improve the condition and function of the ocular surface. These findings also suggest that corneal cell necrosis may occur in some patients who are taking multiple BAC-preserved ocular medications over long periods of time, even when the amount of BAC in any one medication is below the threshold concentration at which necrosis occurs.

It is well known in the reference literature that small organic compounds, such as benzalkonium chloride (BAC), chlorhexidine, thimerosal have excellent antimicrobial activity; however, it is now known that these small organic antimicrobials are often toxic to the sensitive tissues of the eye and can accumulate in cornea, contact lenses, particularly soft, hydrophilic contact lenses. Medications with BAC may cause disruption of the corneal surface with lower concentrations of BAC.

The preservative in Alphagan® P is stabilized chlorine dioxide ("SCD"), an oxidative preservative that was known to be compatible with the eye but Chlorine dioxide is not an ideal preservative ingredient. It is an oxidative preservative and it would oxidize brimonidine. It is difficult to stabilize and is light-sensitive as referred in U.S. Pat. No. 7,265,117.

It has been unexpectedly found that benzododecinium bromide is a quaternary ammonium compound that does not form a precipitation with brimonidine at pH of around 6.0. Benzododecinium bromide forms an ion pair with brimonidine, thereby neutralizing the charge of brimonidine. Thus it was surprising to find that benzododecinium bromide is a quaternary ammonium compound that does not form precipitation with brimonidine. In the same conditions brimonidine forms a hazy solution with benzalkonium chloride.

Hence there is an unmet medical need to prepare a topical ophthalmic solution comprising an alpha-2 adrenergic receptor agonist such as brimonidine tartrate and/or pharmaceutically acceptable excipients wherein it does not comprises a solubility enhancing agent and an oxidative preservative. Instead, when the preservative is included in the said solution, the preservative is preferably benzododecinium bromide. Benzododecinium bromide is an effective preservative for alpha-2 adrenergic receptor agonists (e.g., brimonidine) in acidic conditions.

It was surprisingly found by the inventors of the present invention that the formulation of the present invention has shown statistically significant IOP lowering efficacy when administered to normotensive and water loaded New Zealand white rabbits by ocular route. The onset of statistically significant IOP lowering efficacy was 15 minutes earlier in present invention which is same as compared to Alphagan® P, whereas both the formulations were found to be comparable at each time point observed, which indicates that the IOP lowering efficacy of both test formulations (Alphagan® P and the present invention) were statistically comparable.

OBJECT OF THE INVENTION

The main object of the present invention is to develop an aqueous ophthalmic composition comprising an alpha-2 adrenergic receptor agonist and a non-ionic cellulosic polymer and devoid of anionic cellulosic polymer, the solution having a pH less than 6.5.

Another object of the present invention is to develop an aqueous ophthalmic composition of brimonidine compatible with quaternary ammonium compound used as a preservative other than oxidative preservatives without forming precipitate.

Yet another object of the present invention is to develop a method to prepare an aqueous ophthalmic composition comprising an alpha-2 adrenergic receptor agonist and a non-ionic cellulosic polymer and devoid of anionic cellulosic polymer, wherein the solution having a pH less than 6.5.

Yet another object of the present invention provides a method for reducing intraocular pressure in a patient in need thereof comprising administering an aqueous ophthalmic composition comprising an alpha-2 adrenergic receptor agonist and a non-ionic cellulosic polymer, wherein the solution having a pH less than 6.5.

SUMMARY OF THE INVENTION

The present invention provides an aqueous ophthalmic composition comprising an alpha-2 adrenergic receptor agonist and a non-ionic cellulosic polymer, the solution having a pH less than 6.5. The present invention also provides an aqueous ophthalmic composition comprising an alpha-2 adrenergic receptor agonist and a benzododecinium halide. The present invention also provides a method of reducing intraocular pressure in a patient in need thereof, comprising administering to the patient the composition of the present invention, the administered composition comprising an effective amount of the alpha-2 adrenergic receptor agonist.

The alpha-2 adrenergic receptor agonist preferably comprises brimonidine or a pharmaceutically acceptable salt thereof, preferably brimonidine tartrate. The amount of brimonidine or pharmaceutically acceptable salt thereof is preferably 0.05-0.2% (w/v) brimonidine tartrate, based on brimonidine free base. The alpha-2 adrenergic receptor agonist is dissolved or suspended in the aqueous composition, preferably dissolved.

The non-ionic cellulosic polymer preferably comprises hydroxypropyl methylcellulose, preferably 0.05-1.5% (w/v) hydroxypropyl methylcellulose.

The pH of the composition is preferably less than or up to 6.6. The pH of the composition is preferably at least or greater than 5.5.

The composition preferably comprises a preservative, preferably benzododecinium halide, more preferably benzododecinium bromide. When the preservative is present, the composition preferably comprises 0.005% to 0.03% (w/v) benzododecinium halide, preferably benzododecinium bromide.

The composition preferably does not comprise an anionic solubility enhancing component, and preferably does not comprise carboxymethyl cellulose. The composition preferably does not comprise an oxidative preservative, and preferably does not comprise an oxy-chloro preservative.

Surprisingly the formulation of the present invention is more stable than the commercial product, Alphagan® P.

The present invention provides a topical ophthalmic solution comprising an alpha-2 adrenergic receptor agonist such as brimonidine tartrate and/or pharmaceutically acceptable excipients wherein the ophthalmic solution is soluble enough to achieve therapeutic efficacy at an acidic pH. Preferably, the acidic pH is less than 7, more preferably less than or about 6.7 or 6.5, more preferably less than or about 6.6 or 6.5. Other than physiological considerations (e.g., eye irritation), there is no particular lower limit on the pH. Preferably, the pH is greater than or about 5, more preferably greater than or about 5.25, or 5.5.

More particularly the present invention provides a topical ophthalmic solution comprising an alpha-2 adrenergic receptor agonist such as brimonidine tartrate and/or pharmaceutically acceptable excipients which does not comprises a solubility enhancing agent and an oxidative preservative. When the preservative is included in the said solution, the preservative is quaternary ammonium compound, preferably benzododecinium bromide.

More preferably, benzododecinium bromide is the only quaternary ammonium compound which is included in said solution.

BRIEF DESCRIPTION OF THE ACCOMPANYING DRAWINGS

FIG. 1 shows the intraocular pressure (IOP) lowering effect of Group I (Alphagan® P) and Group II (present invention) on normotensive New Zealand White Rabbits for treated left eye. The other (right) eye is left untreated and serves as control.

FIG. II shows the intraocular pressure (IOP) lowering effect of Group I (Alphagan® P) and Group II (present invention) on New Zealand White Rabbits for treated left eye in water loaded rabbits. The other (right) eye is left untreated and serves as control.

FIG. III shows the total Impurity levels in various brimonidine formulations i.e. commercial (Alphagan® P) and present invention formulation (brimonidine tartarate 0.1%) at 40° C./NMT 25% RH.

DETAILED DESCRIPTION OF THE INVENTION

As used herein, the term "BAC" wherever appears is an abbreviation for "benzalkonium chloride".

As used herein, the "SCD" wherever appears is an abbreviation for "stabilized chlorine dioxide".

As used herein, the "NMT" wherever appears is an abbreviation for "not more than".

As used herein, the "RH" wherever appears is an abbreviation for "relative humidity".

As used herein, the "HPMC" wherever appears is an abbreviation for "hydroxypropyl methyl cellulose".

As used herein, the "IOP" wherever appears is an abbreviation for "intraocular pressure".

Unless indicated otherwise, all ingredient amounts are presented in units of % weight/volume (% w/v).

Brimonidine tartrate is a known compound that can be made by known methods and is commercially available. See, for example, German Patent No. 2,538,620.

In one embodiment of the present invention, an aqueous ophthalmic composition comprising an alpha-2 adrenergic receptor agonist and a non-ionic cellulosic polymer.

In another embodiment of the present invention, an aqueous ophthalmic composition comprising an alpha-2 adrenergic receptor agonist, a non-ionic cellulosic polymer and devoid of anionic cellulosic polymer.

In yet another embodiment of the present invention, an aqueous ophthalmic composition comprising an alpha-2 adrenergic receptor agonist, a non-ionic cellulosic polymer and devoid of anionic cellulosic polymer and oxidative preservative.

In yet another embodiment of the present invention, an aqueous ophthalmic composition comprising an alpha-2 adrenergic receptor agonist, a non-ionic cellulosic polymer and devoid of anionic cellulosic polymer and oxidative preservative, optionally along with a preservative.

In yet another embodiment of the present invention, an aqueous ophthalmic composition comprising an alpha-2 adrenergic receptor agonist and a preservative.

In yet another embodiment of the present invention, an aqueous ophthalmic composition comprising an alpha-2 adrenergic receptor agonist and a preservative and devoid of an anionic solubility enhancing component.

In yet another embodiment of the present invention, an aqueous ophthalmic composition comprising an alpha-2 adrenergic receptor agonist and a preservative and devoid of an anionic solubility enhancing component and oxidative preservative.

In yet another embodiment of the present invention, an aqueous ophthalmic composition comprising an alpha-2 adrenergic receptor agonist and a preservative and devoid of an anionic solubility enhancing component and oxidative preservative, optionally along with a non-ionic cellulosic polymer.

According to the present invention, an alpha-2 adrenergic receptor is selected from Brimonidine or a pharmaceutically acceptable salt or solvate or hydrate thereof.

According to the present invention, a non-ionic cellulosic polymer is selected from hydroxypropyl methylcellulose, hydroxypropyl cellulose, hydroxymethyl cellulose, hydroxyethyl cellulose or combinations thereof. More preferable is hydroxypropyl methylcellulose.

According to the present invention, a preservative is selected from benzododecinium halide, chlorobutanol, sodium perborate, cetrimonium chloride, thiomersal, methyl parahydroxybenzoate, propyl parahydroxybenzoate, sorbic acid and derivatives thereof, polyquaternium ammonium chloride, polyaminopropyl biguanide, phenyl mercuric nitrate, phenyl mercuric acetate, hydrogen peroxide. More preferably is benzododecinium halide. Still more preferable is benzododecinium bromide.

In yet embodiment of the present invention, an aqueous ophthalmic composition comprising a brimonidine in the range of 0.01-0.5 % (w/v), more preferable in the range of 0.05-0.2% (w/v) and a non-ionic cellulosic polymer in the range of 0.05-1.5 % (w/v), more preferable in the range of 0.1-1.0% (w/v).

In yet embodiment of the present invention, an aqueous ophthalmic composition comprising a brimonidine in the range of 0.01-0.5% (w/v), more preferable in the range of 0.05-0.2% (w/v) and non-ionic cellulosic polymer in the range of 0.05-1.5 %(w/v), more preferable in the range of 0.1-1.0% (w/v) along with a preservative in the range of 0.001% to 0.1% (w/v) and more preferable 0.005% to 0.03% (w/v).

The ophthalmic solution of the present invention contains an effective amount of alpha-2 adrenergic agonist, preferably brimonidine. Preferred amounts are at least 0.01%, more preferably at least about 0.02%, more preferably at least about 0.05%, percentages being w/v. Preferred amount are less than about 1.0%, more preferably less than about 0.5%, 0.2%. Some preferred amounts include 0.06%, 0.07%, 0.08%, 0.09%, 0.1%, and 0.15%. Preferred ranges include ranges formed from any two of these amounts. Weight of brimonidine is based on the free base. Salts of brimonidine are included, preferably including brimonidine tartrate.

In an embodiment the present invention provides a topical ophthalmic solution comprising an alpha-2 adrenergic receptor agonist such as brimonidine tartrate and/or pharmaceutically acceptable excipients wherein the ophthalmic solution is at an acidic pH.

In another embodiment the present invention provides a topical ophthalmic solution comprising an alpha-2 adrenergic receptor agonist such as brimonidine tartrate and/or pharmaceutically acceptable excipients which does not comprises a solubility enhancing agent and an oxidative preservative. Instead, when the preservative is included in the said solution, the preservative is a quaternary ammonium compound, preferably benzododecinium halide.

In yet another embodiment benzododecinium halide, preferably benzododecinium bromide is the only quaternary ammonium compound which is included in said solution.

It has been found that benzododecinium halide is a quaternary ammonium compound that does not form a precipitation with brimonidine at pH of around 6.0. Benzododecinium halide (e.g., bromide) forms an ion pair with brimonidine, thereby neutralizing the charge of brimonidine. It had been believed that quaternary ammonium preservatives other that BAC were generally not compatible with brimonidine. Thus it was surprising to find that benzododecinium halide is compatible with brimonidine. In particular, benzododecinium bromide does not form precipitation with brimonidine. The observation that benzododecinium bromide is compatible with brimonidine indicates it should be an effective preservative for various dosage forms comprising brimonidine, including solutions and suspensions.

Multi-use containers preferably comprise a preservative. Single-use containers may optionally comprise preservative. When used, any safe and effective preservative amount of benzododecinium halide, preferably bromide, may be used in compositions of the present invention. Amounts between 0.001% to 0.1% w/v are suitable. An amount of about 0.005% to 0.03% is preferred. A preferred composition comprises about 0.01% (e.g., 0.012%).

As a result of the various studies, it has been found that there is no need to add any solubility enhancing agent because brimonidine is soluble at acidic pH range between about 5.5 to about 6.5.

Compositions of the present invention preferably comprise a non-ionic cellulosic polymer. The non-ionic cellulosic polymer can be any water-soluble polymer that increases the viscosity of the composition. Non-limiting examples include hydroxypropyl methyl cellulose (HPMC), hydroxypropyl cellulose (HPC), hydroxyethyl cellulose, hydroxymethyl cellulose and other modified celluloses. A preferred non-ionic cellulosic polymer is HPMC. Any amount of non-ionic cellulosic polymer may be used to obtain a suitable viscosity. Preferred amounts include at least 0.05%, more preferably at least 0.1% or 0.2%, all percentages being w/v. Preferred amounts include up to 1.5%, more preferably up to 1%. Some preferred amounts include 0.3%, 0.4%, 0.5%, 0.6%, 0.7%, 0.8% and 0.9%. Preferred ranges include ranges formed from any two of these amounts. For the purposes of the present invention, the non-ionic cellulosic polymer does not include carboxymethylcellulose.

Surprisingly the formulation of the present invention is more stable than the commercial product, Alphagan® P. The inventors of the present invention have further studied extensively and completed the present invention. Namely, the present invention relates to:

1. An aqueous ophthalmic composition comprising an alpha-2 adrenergic receptor agonist, a non-ionic cellulosic polymer and devoid of anionic cellulosic polymer, optionally along with a preservative and pharmaceutically acceptable excipients, wherein the pH of said composition is less than 6.5.

2. The composition according to the above 1 wherein the alpha-2 adrenergic receptor agonist is brimonidine or a pharmaceutically acceptable salt or solvate or hydrate thereof.

3. The composition according to the above 1 or 2, wherein the composition comprises 0.01-0.5 (w/v) of brimonidine tartrate.

4. The composition according to the above 1 or 2, wherein the composition comprises 0.05-0.2% % (w/v) of brimonidine tartrate.

5. The composition according to the above 1, wherein the non-ionic cellulosic polymer is selected from the group consist of hydroxypropyl methylcellulose, hydroxypropyl cellulose, hydroxymethyl cellulose, hydroxyethyl cellulose or combinations thereof.

6. The composition according to the above 1 or 5, wherein the non-ionic cellulosic polymer is hydroxypropyl methylcellulose.

7. The composition according to the above 6, wherein the composition comprises of 0.05-1.5 (w/v) hydroxypropyl methylcellulose.

8. The composition according to the above 7, wherein the composition comprises of 0.1-1.0% (w/v) hydroxypropyl methylcellulose.

9. The composition according to the above 1 to 8, wherein the pH is less than 6.5.

10. The composition as claimed in claims 1 to 8, wherein the pH of the composition is in the range of 5.5-6.5.

11. The composition according to the above 1, wherein the preservative is selected from the group consist of benzododecinium halide, chlorobutanol, sodium perborate, cetrimonium chloride, thiomersal, methyl parahydroxybenzoate, propyl parahydroxybenzoate, sorbic acid and derivatives thereof, polyquaternium ammonium chloride, polyaminopropyl biguanide, phenyl mercuric nitrate, phenyl mercuric acetate, hydrogen peroxide.

12. The composition according to the above 1 or 11, wherein the preservative is benzododecinium halide.

13. The composition according to the above 1 or 11, wherein the preservative is benzododecinium bromide.

14. The composition according to the above 1 to 13, wherein the composition is further devoid of an oxidative preservative.

15. A method of reducing intraocular pressure in a patient in need thereof, comprising administering to the patient the composition according to the above 1 to 14, the administered composition comprising an effective amount of the alpha-2 adrenergic receptor agonist.

16. An aqueous ophthalmic composition comprising an alpha-2 adrenergic receptor agonist and benzododecinium halide.

17. The composition according to the above 16, wherein the composition comprises 0.001% to 0.1% (w/v) of benzododecinium halide.

18. The composition according to the above 17, wherein the composition comprises 0.005% to 0.03% (w/v) of benzododecinium halide.

19. The composition according to the above 16 to 18, wherein the benzododecinium halide is benzododecinium bromide.

20. The composition according to the above 16, wherein the alpha-2 adrenergic receptor agonist is brimonidine or a pharmaceutically acceptable salt or solvate or hydrate thereof.

21. The composition according to the above 16, wherein the composition further comprises a non-ionic cellulosic polymer.

22. The composition according to the above 21, wherein the non-ionic cellulosic polymer is selected from the group consist of hydroxypropyl methylcellulose, hydroxypropyl cellulose, hydroxymethyl cellulose, hydroxyethyl cellulose and combinations thereof.

23. The composition according to the above 21 or 22, wherein the non-ionic cellulosic polymer is hydroxypropyl methylcellulose.

24. The composition according to the above 16 to 23, wherein the pH of the composition is in the range of 5.5-6.5.

25. The composition according to the above 16 to 24, wherein the composition is devoid of an anionic solubility enhancing component.

26. The composition according to the above 25, wherein the composition is further devoid of an oxidative preservative.

27. An aqueous ophthalmic composition comprising
  a) brimonidine tartrate in an amount of 0.01-0.5% (w/v);
  b) hydroxypropyl methylcellulose in an amount of 0.1-1.0% (w/v)

c) benzododecinium halide in an amount of 0.001% to 0.1% (w/v) which is devoid of anionic cellulosic polymer, wherein the pH of said composition is less than 6.5.

28. A method of reducing intraocular pressure in a patient in need thereof, comprising administering to the patient the composition according to the above 16 to 27, the administered composition comprising an effective amount of the alpha-2 adrenergic receptor agonist.

29. Use of a composition according to the above 1 to 14 and 16 to 27 for reducing intraocular pressure in a patient in need thereof comprising safe and effective amount of alpha-2 adrenergic receptor agonist.

30. A method for the preparation of an aqueous ophthalmic composition according to the above 1 to 14 and 16 to 27, wherein the method comprises of:

a) Adding required quantity of non-ionic cellulosic polymer to one part of water for injection at 60-70° C. under stirring to form the solution.

b) Cooling the solution as obtained in step a) to room temperature under stirring to form Part-A of the solution.

c) Adding pharmaceutically acceptable excipients as described herein, preservative and alpha-2 adrenergic receptor agonist under stirring to another part of water for injection which is cooled to room temperature before such addition to form Part-B of the solution.

d) Adding Part-B solution to Part-A solution under stirring to form a solution.

e) Checking and adjusting the pH of the solution as obtained in step d) with 1N HCl/1N NaOH and finally making up the volume to 100% with water for injection to obtain an aqueous ophthalmic composition.

In addition to brimonidine or salt thereof, the solution of the present invention preferably also contains buffer components to stabilize or maintain the ophthalmic formulation at the desired pH. Any suitable buffer component can be employed which is compatible with the other ingredients of the ophthalmic solution, and which does not have deleterious or toxic properties which could harm the eye. Examples of suitable ophthalmically acceptable buffer components include acetate buffers, citrate buffers, phosphate buffers, borate buffers and mixtures thereof. Specific buffer components useful in the present invention include boric acid, sodium borate, sodium phosphates, including mono, di- and tri-basic phosphates, such as sodium phosphate monobasic monohydrate and sodium phosphate dibasic heptahydrate, and mixtures thereof.

In an embodiment of the present invention, tonicity adjusting agents may be added and included without limitation such as glycerin, sorbitol, sodium hydroxide, sodium chloride, potassium chloride, and mannitol, dextrose, propylene glycol and combinations thereof or any other suitable ophthalmically acceptable tonicity adjusting agents.

In one embodiment, the tonicity component is selected from inorganic salts and mixtures thereof.

The amount of ophthalmically acceptable tonicity component utilized can vary widely. In one embodiment, the tonicity component is preferably present in the ophthalmic formulation in an amount in the range of about 0.5 to about 0.9 weight/volume percent of the formulation.

Typical of ophthalmically acceptable inorganic salt tonicity components are alkali metal chlorides and alkaline earth metal chlorides, such as sodium chloride, potassium chloride, calcium chloride and magnesium chloride.

The pH adjusting agents include hydrochloric acid, sodium hydroxide, phosphoric acid, acetic acid and the like.

In another embodiment one or more additional components can be included in the present solution based on the particular application for which the formulations are made. The additional component or components included in the present solution are chosen to impart or provide at least one beneficial or desired property to the solutions. Examples of such additional components include cleaning agents, non-ionic polymers, nutrient agents, sequestering agents, viscosity builders, contact lens conditioning agents, antioxidants, and the like.

These additional components are each included in the present ophthalmic solution in an amount effective to impart or provide the beneficial or desired property to the compositions.

Exemplary non-ionic polymers include, but are not limited to, Povidone (PVP: polyvinyl pyrrolidone), polyvinyl alcohol, copolymer of PVP and polyvinyl acetate, gelatin, polyethylene oxide, acacia, dextrin, starch, polyhydroxyethylmethacrylate (PHEMA), water soluble nonionic polymethacrylates and their copolymers, modified non-cellulosic polysaccharides, nonionic gums, nonionic polysaccharides, and/or mixtures thereof, such as referred in US20130287821 and EP2659881.

Examples of useful sequestering agents include disodium ethylene diamine tetraacetate, alkali metal hexametaphosphate, citric acid, sodium citrate and mixtures thereof.

Examples of useful viscosity builders include hydroxyethyl cellulose, hydroxymethyl cellulose, HPMC (hydroxypropyl methylcellulose), polyvinyl pyrrolidone, polyvinyl alcohol and mixtures thereof.

Examples of useful antioxidants include sodium metabisulfite, sodium thio sulfate, N-acetylcysteine, butylated hydroxyanisole, butylated hydroxytoluene, sodium sulfite, potassium sulpfite, sodium metabisulfite, sodium thiosulfate and mixtures thereof.

The excipients used in the present invention are preferably selected to be non-toxic and have no substantial detrimental effect (preferably, in the amount used) on the present ophthalmic solutions, on the use of the solutions or on the human or animal to which the ophthalmic compositions are to be administered.

In an embodiment, the present invention provide the ophthalmic compositions in the form of aqueous liquids, solutions, emulsion, dispersion, suspension, reverse emulsion and microemulsion, nanoemulsion, nano reservoir system, in-situ gel drops, nanoparticulate system, liposomal drops, bioadhesive gel drops, drops and the like.

In another embodiment, the present invention preferably provides the ophthalmic solution for topical ophthalmic delivery comprising administering said solution in the eyes, ear, and/or nose of the humans or animals.

In yet another embodiment, the stable, solution would be an aqueous solution having a pH value within the range of from about 5.5 to about 6.5 and osmolality in range of at least about 200 mOsmol/kg, preferably in the range of about 200 to about 350 or about 400 mOsmol/kg.

In further embodiment, the present invention provides a process of preparing a stable, ophthalmic solution comprising brimonidine tartrate and/or pharmaceutically acceptable excipients, that is more stable than the commercial product, Alphagan® P. stability data is shown in stability section.

Still further, the present invention may also be presented as a kit comprising a stable, aqueous solution comprising brimonidine tartrate and/or pharmaceutically acceptable excipients, the aqueous solution being contained within a container prepared from a pharmaceutically acceptable packaging material.

Any pharmaceutically acceptable packaging material may be use, preferably packaging material that is suitable for containing ophthalmic aqueous solution, more preferably brimonidine tartrate ophthalmic aqueous solution. Pharmaceutically acceptable packaging materials include but are not limited to low density polyethylene ("LDPE"), high density polyethylene ("HDPE"), polypropylene, polystyrene, polycarbonate, polyesters (such as polyethylene terephthalate and polyethylene naphthalate), nylon, polyvinyl chloride), poly(vinylidine chloride), poly(tetrafluoroethylene) and other materials known to those of ordinary skill in the art. Flexible bottles prepared from, or comprising, LDPE, HDPE or polypropylene are particularly preferred.

The present invention provides a method to lower intraocular pressure in patients with glaucoma or ocular hypertension wherein the method comprises a topical application to the eye of the patient in need of a topical ophthalmic solution comprising an alpha-2 adrenergic receptor agonist such as brimonidine tartrate and/or pharmaceutically acceptable excipients.

The present invention provides a method of using the inventive ophthalmic solution for lowering intraocular pressure in patients with glaucoma or ocular hypertension.

The present invention provides a process of preparing a topical ophthalmic solution comprising an alpha-2 adrenergic receptor agonist such as brimonidine tartrate and/or pharmaceutically acceptable excipients.

The term preservative used in this invention has the meaning commonly understood in the ophthalmic art. The preservatives comprises one or more of benzalkonium chloride, benzyldodecinium bromide, chlorobutanol, sodium perborate, cetrimonium chloride, thiomersal, methyl para-hydroxybenzoate, propyl parahydroxybenzoate, sorbic acid and derivatives thereof, polyquaternium ammonium chloride, polyaminopropyl biguanide, phenyl mercuric nitrate, phenyl mercuric acetate, hydrogen peroxide and the like.

The amount of preservative to be included in the compositions of the present invention will generally range from 0.001 to 0.03%, preferably 0.001 to 0.015%.

One particularly suitable preservative for use in the compositions of the present invention is benzododecinium bromide.

EXAMPLES

The scope of the present invention is illustrated by the following example which is not meant to restrict the scope of the invention in any manner whatsoever.

The term 'q.s.' wherever appears in the examples is an abbreviation for 'quantity sufficient' which is the amount of the excipient in such quantities that is just sufficient for its use in the composition of the present invention.

Example 1

| Ingredients | Present Invention % w/v |
| --- | --- |
| Brimonidine Tartrate | 0.1 |
| HPMC (E4M) | 0.5 |
| Boric acid | 1.1 |
| Sodium borate | 0.07 |
| Sodium chloride | 0.18 |
| Potassium chloride | 0.14 |
| Calcium chloride | 0.02 |
| Magnesium chloride | 0.006 |

-continued

| Ingredients | Present Invention % w/v |
| --- | --- |
| Benzododecinium bromide | 0.012 |
| Hydrochloric acid | q.s. to adjust pH (approx. 6) |
| Sodium hydroxide | q.s. to adjust pH (approx. 6) |
| Milli-Q water | q.s. to 1 mL |

Example 2

| Ingredients | Present Invention % w/v |
| --- | --- |
| Brimonidine Tartrate | 0.15 |
| HPMC (E4M) | 0.5 |
| Boric acid | 1.1 |
| Sodium borate | 0.07 |
| Sodium chloride | 0.18 |
| Potassium chloride | 0.14 |
| Calcium chloride | 0.02 |
| Magnesium chloride | 0.006 |
| Benzododecinium bromide | 0.012 |
| Hydrochloric acid | q.s. to adjust pH (approx. 6) |
| Sodium hydroxide | q.s. to adjust pH (approx. 6) |
| Milli-Q water | q.s. to 1 mL |

Manufacturing Process:
I. Part A—(Preparation of hydroxypropyl methylcellulose (HPMC) solution)
  1. Add required quantity of HPMC to water for injection (WFI) (40% of batch size) at 60-70° C. under stirring.
  2. Cool this solution up to room temperature (up to 25° C.) under stirring.
II. Part B—(Preparation of API solution)
  1. Take water for injection (50% of batch size) in clean container.
  2. Cool water for injection up to room temperature (up to 25° C.).
  3. Add and dissolve Boric Acid in above water for injection under stirring.
  4. Add and dissolve Sodium Borate to step 3 under stirring.
  5. Add and dissolve Sodium Chloride to step 4 under stirring.
  6. Add and dissolve Potassium Chloride to step 5 under stirring.
  7. Add and dissolve Calcium Chloride to step 6 under stirring.
  8. Add and dissolve Magnesium Chloride to step 7 under stirring.
  9. Add and dissolve Benzododecinium Bromide to step 8 under stirring.
  10. Add and dissolve Brimonidine Tartrate to step 9 under stirring.
III. Add Part-B (API solution) to Part-A (HPMC Solution) under stirring.
IV. Check the pH of above solution and adjust the pH of solution with IN hydrochloric acid/1N sodium hydroxide solution.
V. Make up the volume up to 100% with water for injection (WFI).

Stability Studies:

Stable, topical ophthalmic solutions comprising an alpha-2 adrenergic receptor agonist such as brimonidine tartrate and/or pharmaceutically acceptable excipients are prepared as shown in Table 2 and exposed to accelerated conditions at 40±2° C. and relative humidity of NMT 25% RH for 1, 2, 3 and 6 months to determine the stability of the present invention as shown in Table 4. An initial study of commercially available Alphagan® P is initiated to demonstrate the physico-chemical parameters as shown in Table 3.

TABLE 2

| Ingredients | Present Invention % w/v |
|---|---|
| Brimonidine Tartrate | 0.1 |
| HPMC (E4M) | 0.5 |
| Boric acid | 1.1 |
| Sodium borate | 0.07 |
| Sodium chloride | 0.18 |
| Potassium chloride | 0.14 |
| Calcium chloride | 0.02 |
| Magnesium chloride | 0.006 |
| Benzododecinium bromide | 0.012 |
| Hydrochloric acid | q.s. to adjust pH (approx. 6) |
| Sodium hydroxide | q.s. to adjust pH (approx. 6) |
| Milli-Q water | q.s. to 1 mL |

Results and Observations:

The formulation of Alphagan® P is evaluated to demonstrate the physico-chemical parameters such as brimonidine tartrate content and related substances for accelerated conditions at 40±2° C. and relative humidity of NMT 25% RH. Results are shown in Table 3.

Initial Testing of Commercial Product:

TABLE 3

| | Parameters | Commercial product (Alphagan ® P) | Commercial product (Alphagan ® P) |
|---|---|---|---|
| | Description | Clear, greenish yellow colored solution | Clear, greenish yellow colored solution |
| | pH | 7.60 | 7.60 |
| | Osmolality | 265 mOsmol/Kg | 266 mOsmol/Kg |
| | Viscosity | 3.05 cps | 3.13 cps |
| | Assay of Brimonidine Tartrate | 96.2% | 96.2% |
| | Related Substances | | |
| a | Debromobrimonidine | — | — |
| b | 6-Amino-quinoxalina | ND | ND |
| c | 5-Bromoquinoxaline-6-Amine | ND | ND |
| d | Highest Unknown Impurity | 1.49% | 1.43% |
| e | Other Unknown Impurity | 1.16% | 1.43% |
| f | Total Impurities | 2.65% | 2.86% |

The ophthalmic solution of present invention is evaluated to demonstrate the physico-chemical parameters such as brimonidine tartrate content and related substances at 1, 2, 3 and 6 months for accelerated conditions at 40±2° C. and relative humidity of NMT 25% RH. Results are shown in Table 4.

TABLE 4

Stability Data of Brimonidine Tartrate Ophthalmic Solution of the present invention:

Batch No. PR3F044-06

| | Parameters | Initial | 1 Month | 2 Month | 3 Month | 6 Month |
|---|---|---|---|---|---|---|
| | | | 40 ± 2° C./NMT 25% RH | | | |
| | Description | Clear, greenish yellow colored solution | Clear, slightly greenish yellow colored solution | Clear, slightly greenish yellow colored solution | Clear, slightly greenish yellow colored solution | Clear, slightly greenish yellow colored solution |
| | pH | 6.04 | 5.92 | 5.99 | 5.92 | 5.56 |
| | Osmolality | 283 mOsmol/Kg | 281 mOsmol/Kg | 279 mOsmol/Kg | 293 mOsmol/Kg | 302 mOsmol/Kg |
| | Viscosity | 17.5 cps | 17.0 cps | 16.2 cps | 15.7 cps | 14.7 cps |
| | Assay of Brimonidine Tartrate | 96.0% | 99.7% | 99.8% | 99.3% | 101.0% |
| | Content of Benzododecinium Bromide | 91.0% | 88.8% | 92.3% | 90.3% | 87.7% |
| | Related Substances | | | | | |
| a | Debromobrimonidine | ND | 0.01% | 0.01% | 0.01% | 0.29% |
| b | 6-Amino-quinoxalina | ND | ND | ND | ND | ND |
| c | 5-Bromoquinoxaline-6-Amine | ND | 0.02% | 0.02% | 0.04% | 0.10% |
| d | Highest Unknown Impurity | 0.03% | 0.03% | 0.05% | 0.09% | 0.014% |
| e | Other Unknown Impurity | 0.03% | ND | 0.04% | 0.11% | 0.12% |
| f | Total Impurities | 0.03% | 0.06% | 0.12% | 0.25% | 0.65% |

The Results at Accelerated Conditions at 40±2° C. and Relative Humidity of NMT 25% RH for Alphagan® P as a Commercial Product:

The brimonidine tartrate content is measured and found to be 96.2% (Limit: 90.0-110.0%) which is within the acceptable limit range, the highest unknown impurity is measured and found to be 1.49% (Limit: NMT 1.0%) which is above the acceptable limit range and total impurity is measured and found to be 2.65% (Limit: NMT 3.0%) which is within the acceptable limit range.

The Results at Accelerated Conditions at 40±2° C. and Relative Humidity of NMT 25% RH for 6 Months for the Present Invention:

The brimonidine tartrate content is measured and found to be 101% (Limit: 90.0-110.0%) which is within the acceptable limit range, the highest unknown impurity is measured and found to be 0.014% (Limit: NMT 1.0%) which is within the acceptable limit range and total impurity is measured and found to be 0.65% (Limit: NMT 3.0%) which is within the acceptable limit range.

The above stability study of the present invention indicates that the all the parameters of the present invention are well within narrow limits and the solution prepared by the present invention formulation is stable with respect to all physico-chemical parameters which indicate that at stability testing conditions there appears to be no considerable degradation in the present solution.

Comparison of Impurity Profile of Commercial Product (Alphagan® P) and Present Invention Formulation (Brimonidine Tartarate 0.1%):

Further the two (2) lots of Commercial product {Alphagan® P (0.1%)} and four (4) lots of present invention formulation (brimonidine tartarate 0.1%) are compared at accelerated stability conditions (40° C./NMT 25% RH) and then compared the Impurity profiles of the two and the results are tabulated in Tables 5 and Table 6.

TABLE 5

(Commercial product {Alphagan ® P (0.1%)})

| Related substances/Impurity | Commercial product {Alphagan ® P (0.1%)} | | | | | | | | | |
|---|---|---|---|---|---|---|---|---|---|---|
| | Lot No-79087 | | | | | Lot No-77611 | | | | |
| | Initial | 1 M | 2 M | 3 M | 6 M | Initial | 1 M | 2 M | 3 M | 6 M |
| Debromobrimonidine | 0.01 | 0.01 | 0.02 | 0.02 | 0.03 | 0.01 | 0.01 | 0.02 | 0.02 | 0.02 |
| 6-Amino-quinoxaline | ND | ND | ND | 0.01 | ND | ND | ND | ND | ND | ND |
| 5-Bromoquinoxaline-6-amine | 0.03 | 0.08 | 0.11 | 0.17 | 0.35 | 0.03 | 0.06 | 0.13 | 0.24 | 0.52 |
| Highest Unknown Impurity | 0.30 | 0.60 | 0.86 | 1.18 | 1.85 | 0.26 | 0.58 | 0.91 | 1.33 | 1.12 |
| Unknown Impurity | 0.58 | 0.62 | 0.63 | 0.6 | 1.06 | 0.49 | 0.64 | 0.92 | 0.96 | 2.17 |
| Total Impurity | 0.92 | 1.31 | 1.62 | 1.98 | 3.29 | 0.79 | 1.29 | 1.98 | 2.55 | 3.83 |

TABLE 6

{Present invention formulation (brimonidine tartarate 0.1%)}

| Related substances/Impurity | {Present invention formulation (brimonidine tartarate 0.1%)} | | | | | | | | | |
|---|---|---|---|---|---|---|---|---|---|---|
| | PR3F044-06 | | | | | PR3F044-22 | | | | |
| | Initial | 1 M | 2 M | 3 M | 6 M | Initial | 1 M | 2 M | 3 M | 6 M |
| Debromobrimonidine | *ND | 0.01 | 0.01 | 0.01 | 0.29 | BQL | BQL | 0.02 | 0.15 | 0.04 |
| 6-Amino-quinoxaline | ND | ND | ND | ND | ND | ND | ND | ND | BQL | 0.01 |
| 5-Bromoquinoxaline-6-amine | ND | 0.02 | 0.02 | 0.04 | 0.1 | ND | 0.01 | 0.02 | 0.05 | ND |
| Highest Unknown Impurity | 0.03 | 0.03 | 0.05 | 0.09 | 0.14 | BDL | BDL | 0.09 | 0.13 | 0.49 |
| Unknown Impurity | 0.03 | ND | 0.04 | 0.11 | 0.12 | ND | BDL | 0.15 | 0.11 | 0.66 |
| Total Impurity | 0.03 | 0.06 | 0.12 | 0.25 | 0.65 | BDL | 0.01 | 0.28 | 0.44 | 1.2 |

| Related substances/Impurity | {Present invention formulation (brimonidine tartarate 0.1%)} | | | | | | | | | |
|---|---|---|---|---|---|---|---|---|---|---|
| | PR3F044-31 | | | | | PR3F044-32 | | | | |
| | Initial | 1 M | 2 M | 3 M | 6 M | Initial | 1 M | 2 M | 3 M | 6 M |
| Debromobrimonidine | **BQL | 0.02 | 0.03 | 0.04 | Ongoing | BQL | 0.02 | 0.04 | 0.05 | Ongoing |
| 6-Amino-quinoxaline | ND | BQL | ND | BQL | | ND | BQL | ND | BQL | |
| 5-Bromoquinoxaline-6-amine | ND | ND | 0.01 | 0.01 | | ND | 0.01 | 0.01 | 0.02 | |

TABLE 6-continued

{Present invention formulation (brimonidine tartarate 0.1%)}

| Highest Unknown Impurity | ***BDL | 0.06 | 0.1 | 0.14 | BDL | 0.06 | 0.1 | 0.14 |
|---|---|---|---|---|---|---|---|---|
| Unknown Impurity | BDL | ND | BDL | BDL | BDL | ND | BDL | BDL |
| Total Impurity | BDL | 0.08 | 0.14 | 0.19 | BDL | 0.09 | 0.15 | 0.21 |

*ND—Not Detected
**BQL—Below Quantitation Limit
***BDL—Below Disregard Limit.

The total Impurity levels in various brimonidine formulations i.e. Commercial product (Alphagan® P) and present invention formulation (brimonidine tartarate 0.1%) at 40° C./NMT 25% RH are tabulated in Table 7 and as plotted in Figure III:

TABLE 7

Total Impurity Level (%)

| | Commercial product (Alphagan ® P) | | Present invention formulations | | | |
|---|---|---|---|---|---|---|
| Time (months) | Alphagan ® P 79087 | Alphagan ® P 77611 | Present Invention-06 | Present Invention-22 | Present Invention-31 | Present Invention-32 |
| 0 | 0.92 | 0.79 | 0.03 | BDL | BDL | BDL |
| 1 | 1.31 | 1.29 | 0.06 | 0.01 | 0.08 | 0.09 |
| 2 | 1.62 | 1.98 | 0.12 | 0.28 | 0.14 | 0.15 |
| 3 | 1.98 | 2.55 | 0.25 | 0.44 | 0.19 | 0.21 |
| 6 | 3.29 | 3.83 | 0.65 | 1.2 | | |

ANIMAL EFFICACY STUDIES: Two studies were conducted to compare the efficacy of the present invention formulation with the commercial product (Alphagan® P) in two different models:
1. Normotensive model
2. Water loaded model.
1. Normotensive Model:
Objective The objective of the study is to test and compare the IOP lowering efficacy of two formulations (Present Invention and commercial product) on normotensive New Zealand white rabbits.
Materials and Methods Twelve adult female New Zealand white rabbits are selected for this study. Body weights of all 12 rabbits are within ±20% of the mean body weight at the time of randomization. The selected animals are randomly grouped into two groups having 6 animals per group. Group I is treated with Alphagan® P and Group II is treated with another formulation (Present Invention), topically in left eye. The other (right) eye is left untreated and serves as control.
Dose level 50 L of each formulation was instilled once in left eye.
Test After randomization and grouping, intra ocular pressure is measured initially for 24 hours at 2 hours interval to observe the degree of diurnal variations. On day 1 of experiment, baseline IOP is measured for both eyes of each animal. After baseline estimation, the commercial formulation (SRC/Aravali/78115) is instilled in left eye of all rabbits in group I and another present invention formulation (SRC/Aravali/022) in group II. The contra lateral eye serves as control.

Subsequent to the test item instillation, IOP estimations are repeated at 1 hr intervals until the baseline IOP is achieved.

Observations:

Cageside Observations & Physical Examinations

All the animals are observed for cageside observations and physical examinations for 2 days for each group.
Mortality All the animals are observed for mortality for 2 days of experiment.

Intra Ocular Pressure Measurement

After randomization and grouping, and before initiating the experiment, intra ocular pressure is measured initially for 24 hours at 2 hours interval to observe the degree of diurnal variations. On the testing day before the instillation of test item IOP is measured to determine the baseline IOP and after every 1 hour interval after dosing till the baseline IOP is achieved.

Interpretation of Results:

IOP readings of formulations instilled in the left eye of each animal are compared for IOP lowering efficacy with respect to the extent and duration within its own group. At the same time IOP lowering ability of both formulations is compared between the groups of animals i.e. commercial formulation (SRC/Aravali/78115) and present invention formulation (SRC/Aravali/022). To derive the statistical significance, Student's t test is used for IOP data. The statistical significance is disclosed at 95% confidence interval ($p<0.05$).

Results and Discussion:

Cageside Observations & Physical Examinations

All the animals are normal in appearance throughout the observation period. The cageside observations and physical examinations data are reported in Table 8.

TABLE 8

Cage side observations & physical examinations

| Group No. | No. of animals used | Clinical sign | Cage side observations & physical examination Day 0 | Day 1 |
|---|---|---|---|---|
| I | 6F | Normal | 6 of 6 | 6 of 6 |
| II | 6F | Normal | 6 of 6 | 6 of 6 |

Mortality

There is no mortality observed in both dose groups. The mortality data is reported in Table 9.

TABLE 9

Mortality

| Group No. | No. of animals used | Mortality Day 0 | Day 1 |
|---|---|---|---|
| I | 6F | 0/6 | 0/6 |
| II | 6F | 0/6 | 0/6 |

Intra Ocular Pressure Measurement

Diurnal intra ocular pressure measured for 24 hr (at 2 hr interval) does not have any statistically significant (p<0.05) difference among left and right eyes of animals within the group for both groups. Intraocular pressure for left eye of Groups I and II are also comparable and this is also true for right eye of both groups.

Before test item instillation baseline IOP is measured and then for the next 5 hrs at 1 hr intervals. Peak statistically significant (p<0.05) drop of IOP in Groups I & II is observed at 2nd hour of instillation as compare to control eye. When particular time point is compared with baseline statistically significant difference is observed at 2nd and 3rd hour in both groups.

At the same time, IOP readings of animals from Group I are compared with animals of Group II and there are no statistically significant changes observed. The extent and duration of IOP lowering effect of two formulations {commercial product (Alphagan® P) and present invention} are comparable.

Based on observations obtained from the present study, it is concluded that two formulations {commercial product (Alphagan® P) and present invention} have statistically significant IOP lowering effect.

The intra ocular pressure data for Normotensive Model is reported in Table 10 and presented in Figure I.

TABLE 10

Intra ocular pressure (mmHg)
Baseline & after instillation

| Group | Eye | | Baseline | 1 hr | 2 hr | 3 hr | 4 hr | 5 hr |
|---|---|---|---|---|---|---|---|---|
| I | Left | Mean | 21.0 | 20.1 | 14.5 | 16.4 | 19.0 | 20.3 |
| | | SEM | 0.9 | 0.7 | 0.7 | 0.6 | 0.7 | 0.6 |
| | | P VALUE (BL Vs. time) | — | 0.56 | 0.00 | 0.00 | 0.11 | 0.55 |
| | Right | Mean | 20.3 | 19.8 | 19.8 | 18.2 | 20.6 | 20.9 |
| | | SEM | 0.3 | 0.7 | 1.0 | 0.9 | 0.5 | 0.5 |
| | | P VALUE (BL Vs. time) | — | 0.51 | 0.63 | 0.05 | 0.59 | 0.35 |
| II | Left | Mean | 20.0 | 19.2 | 15.7 | 16.0 | 19.3 | 20.9 |
| | | SEM | 0.4 | 0.5 | 0.6 | 0.9 | 0.8 | 0.5 |
| | | P VALUE (BL Vs. time) | — | 0.21 | 0.00 | 0.00 | 0.37 | 0.20 |
| | Right | Mean | 18.9 | 17.9 | 19.1 | 17.4 | 20.3 | 19.8 |
| | | SEM | 0.6 | 0.7 | 1.0 | 0.8 | 0.3 | 0.4 |
| | | P VALUE (BL Vs. time) | — | 0.27 | 0.92 | 0.15 | 0.06 | 0.28 |

N = 6 animals per group;
SEM = Standard Error of Mean;
BL = Baseline.

Conclusion:

Based on the observations obtained from this study, it is concluded that the two formulations, {commercial product (Alphagan® P) and present invention} show statistically significant IOP lowering effect when administered to New Zealand white rabbits and the efficacy of both the formulations is statistically comparable.

2. Water Loaded Model:

Objective

The objective of the study is to test and compare the TOP lowering efficacy of two different formulations on water loaded New Zealand white rabbits.

Materials and Methods

Twelve adult female New Zealand white rabbits those used in normotensive study are used for this study. The animals are randomly grouped into two different groups containing 6 animals per group at the time of randomization in normotensive study. Group I is treated with commercial product (Alphagan® P) and Group II is treated with another present invention formulation, topically in left eye. Same grouping is followed for both the dose groups as followed in normotensive study.

Dose level

50 L of each formulation is instilled once in left eye.

Test

After weighing, the baseline IOP is noted and rabbits are first orally administered with water @ 70 mL/kg through orogastric tube and IOP is measured till the baseline IOP achieved (for 2.5 hrs) at 0.25 hr interval to observe the IOP pattern. The time at which the peak IOP is achieved is noted.

On the next day of experiment, initially baseline IOP is measured for both eyes. After the baseline estimation, commercial product (Alphagan® P) formulation is instilled in left eye of all rabbits in Group I and present invention in Group II. The right eye serves as control.

Test item instillation is followed by rapid oral administration of water (70 mL/kg) through an orogastric tube.

The interval between drug administration and water loading is kept at 1.5 hr based on the following observations, time to peak intraocular pressure lowering effect of the drug as observed in normotensive rabbit study numbered 132101 (2 hrs) and the time of peak IOP elevation observed in water loaded untreated rabbits (15 min to 90 min) in this study numbered 132102. Afterwards, IOP estimations are carried out for 2.25 hours at 0.25 hr interval till the IOP returns to original baseline IOP.

Observations

Cageside Observations & Physical Examinations

All the animals are observed for cageside observations & physical examinations for 2 days for each group.

Mortality

All the animals are observed for mortality for 2 days of experiment.

Intra Ocular Pressure Measurement

After weighing of animals, the baseline IOP is measured and then rabbits are orally administered with water @ 70 mL/kg through orogastric tube and IOP is measured till the baseline IOP achieved (for 2.5 hrs) at 0.25 hr interval to observe the IOP pattern. The time at which the peak IOP achieved is noted.

On the day of test item instillation, IOP is measured prior to the test item instillation for baseline IOP estimation. After baseline IOP measurement, test items are instilled to respective group, which is followed by rapid oral water loading. IOP estimations are measured at every 0.25 hour interval after water loading till the baseline TOP is achieved.

Interpretation of Results

IOP readings of the test item instilled in the left eye of each animal are compared for TOP lowering effect with respect to the extent and duration within its own group. At the same time IOP lowering ability of both test items is compared in two groups of animal's i.e. commercial product (Alphagan® P) formulation and present invention groups. To derive the statistical significance, Student's t test is used for IOP data. The statistical significance is disclosed at 95% confidence interval (p<0.05).

Results and Discussion

Cageside Observations & Physical Examinations

All the animals are normal in appearance throughout the observation period. The cageside observations and physical examinations data are reported in Table 11.

TABLE 11

Cage side observations & physical examinations

| Group No. | No. of animals used | Clinical sign | Cage side observations & physical examination | |
|---|---|---|---|---|
| | | | Day of water leading only | Day of instillation & water loading |
| I | 6F | Normal | 6 of 6 | 6 of 6 |
| II | 6F | Normal | 6 of 6 | 6 of 6 |

Mortality

There is no mortality observed in both dose groups. The mortality data are reported in Table 12.

TABLE 12

Mortality

| Group No. | No. of animals used | Mortality | |
|---|---|---|---|
| | | Day of water loading only | Day of instillation & water loading |
| I | 6F | 0/6 | 0/6 |
| II | 6F | 0/6 | 0/6 |

Intra Ocular Pressure Measurement

On first day, initially baseline IOP is measured and then rabbits are administered with water @ 70 mL/kg through orogastric tube and IOP is measured till the baseline IOP achieved (for 2.5 hrs) at 0.25 hr interval to observe the IOP pattern. Statistically significant (p<0.05) increased intraocular pressure is observed from 15 min to 90 min in both eyes of rabbits from Group I, from 15 min to 75 min in left eye and 15 min to 90 min in right eye of rabbits from Group II as compared to its baseline reading. At the same time, when within the group left eyes are compared with right eyes, it shows comparable increase in IOP and no statistically significant (p<0.05) changes in IOP is observed for both dose groups. Same way, when left and right eyes of Group I are compared with left and right eyes of Group II, there are no statistically significant (p<0.05) changes observed in IOP, except significant higher IOP is observed in left eye of Group I at baseline and 15 minutes as compare to left eye of Group II, which is believed attributable to biological variation.

On the next day, test items are instilled in left eye of respective groups after baseline IOP measurement. 1.5 hours after test item instillation, animals are orally dosed rapidly with 70 mL/kg of water. This time gap is derived from time to peak intraocular pressure lowering effect of the drug observed in normotensive rabbit study numbered 132101 which was 2 hr and the time of peak IOP elevation observed in water loaded untreated animals (15 min-90 min) in this study numbered 132102.

As compare to baseline, there is a statistically significant (p<0.05) increase in IOP at 15 min in left eyes of both dose groups, at 15 to 75 min in right eye of Group I and at 15 to 105 min in right eye of Group II. In left eyes (treated eyes) of both dose groups, from 30 min onward IOP is reduced and becomes statistically non-significant (p<0.05) as compared to baseline.

At the same time, when both left and right eyes are compared, there is statistically significant (p<0.05) lower IOP observed in left eyes as compared to right eyes from 30 min to 75 min in Group I and from 15 min to 105 min in Group II.

Same way, when left and right eyes of Group I are compared with left and right eyes of Group II, there are no statistically significant (p<0.05) changes observed in IOP, except significant (p<0.05) slight higher IOP observed at 90 minute in left eyes of Group I as compared to left eyes of Group II. This difference might be due to difference in baseline of left eyes of both groups and considered as biological variation.

Lower IOP levels in left eyes of rabbits belonging to both dose groups indicate desired IOP lowering efficacy of both test items. Also, IOP levels in left eyes of both dose groups are comparable hence it can be concluded that the effect of both test items are equivalent to each other. The extent and duration of present invention is longer by 0.5 hour than commercial product (Alphagan® P) formulation as Group II reveals IOP lowering effect up to 105 min as compare to Group I, which reveals IOP lowering effect up to 75 min and response to present invention started 15 min earlier as compare to commercial product (Alphagan® P) formulation when compared to right eyes of respective groups.

Based on observations obtained from present study, it is concluded that two formulations {commercial product (Alphagan® P) formulation and present invention} have statistically significant IOP lowering efficacy and are comparable to each other. Present invention reveals slightly longer duration of action than the commercial product (Alphagan® P) formulation, when compared to right eyes of respective groups.

The intra ocular pressure data for Water Loaded Model are reported in Table 13 and presented in Figure II.

TABLE 13

Intra ocular pressure (mmHg)
Baseline & after instillation

| Group | Eye | | 9:30 Baseline | 12:45 15 min | 13:00 30 min | 13:15 45 min | 13:30 60 min | 13:45 75 min | 14:00 90 min | 14:15 105 min | 14:30 120 min | 14:45 135 min |
|---|---|---|---|---|---|---|---|---|---|---|---|---|
| I | Left | Mean | 19.8 | 24.9 | 21.3 | 20.7 | 18.2 | 18.7 | 19.8 | 19.5 | 19.5 | 18.9 |
| | | SEM | 0.4 | 1.3 | 1.1 | 0.8 | 0.8 | 0.7 | 0.6 | 0.6 | 0.6 | 0.0 |
| | | P VALUE (BL Vs. time) | — | 0.00 | 0.21 | 0.31 | 0.12 | 0.19 | 0.98 | 0.70 | 0.70 | 0.05 |
| | Right | Mean | 19.2 | 27.5 | 27.5 | 27.8 | 25.1 | 23.7 | 21.2 | 20.8 | 20.7 | 20.4 |
| | | SEM | 0.7 | 2.2 | 2.3 | 2.0 | 1.8 | 1.8 | 1.6 | 1.2 | 0.9 | 0.7 |
| | | P VALUE (BL Vs. time) | — | 0.00 | 0.01 | 0.00 | 0.01 | 0.04 | 0.29 | 0.30 | 0.22 | 0.26 |
| II | Left | Mean | 18.9 | 21.6 | 19.0 | 19.2 | 17.4 | 17.9 | 17.4 | 17.9 | 18.9 | 19.2 |
| | | SEM | 0.4 | 0.9 | 0.9 | 0.5 | 0.6 | 0.7 | 0.5 | 0.5 | 0.4 | 0.5 |
| | | P VALUE (BL Vs. time) | — | 0.02 | 0.91 | 0.68 | 0.07 | 0.22 | 0.05 | 0.14 | 1.00 | 0.68 |
| | Right | Mean | 19.2 | 26.1 | 25.5 | 25.5 | 24.9 | 23.2 | 22.2 | 20.9 | 20.7 | 20.3 |
| | | SEM | 0.3 | 1.5 | 2.1 | 2.0 | 1.0 | 1.0 | 0.9 | 0.7 | 0.8 | 0.5 |
| | | P VALUE (BL Vs. time) | | 0.00 | 0.01 | 0.01 | 0.00 | 0.00 | 0.01 | 0.04 | 0.12 | 0.09 |

N = 6 animals per group;
SEM = Standard Error of Mean;
BL = Baseline.

CONCLUSION

Based on the observations obtained from this study, it is concluded that the two formulations, commercial product (Alphagan® P) formulation and the present invention, demonstrate statistically significant IOP lowering efficacy when administered to water loaded New Zealand white rabbits by ocular route. The onset of statistically significant IOP lowering efficacy is 15 minutes earlier in present invention as compared to commercial product (Alphagan® P) formulation, whereas both the formulations are found to be comparable at each time point observed, which indicates that the IOP lowering efficacy of both test formulations (commercial product (Alphagan® P) formulation and present invention) are statistically comparable.

The invention claimed is:

1. An aqueous ophthalmic composition comprising
    a) brimonidine tartrate in an amount of 0.01-0.5% (w/v);
    b) hydroxypropyl methylcellulose in an amount of 0.1-1.0% (w/v); and
    c) benzododecinium halide in an amount of 0.001% to 0.1% (w/v) which is devoid of anionic cellulosic polymer, wherein the pH of said composition is less than 6.5.

2. A method of reducing intraocular pressure in a patient in need thereof, comprising administering to the patient a therapeutically effective amount of the composition of claim 1.

* * * * *